United States Patent [19]

Girot et al.

[11] Patent Number: 4,590,424
[45] Date of Patent: May 20, 1986

[54] DETECTION OF ION CONCENTRATION IN A LIQUID

[75] Inventors: Pierre Girot, Paris; Egisto Boschetti, Chatou, both of France

[73] Assignee: Pharmuka Laboratoires, Gennevilliers, France

[21] Appl. No.: 535,307

[22] Filed: Sep. 23, 1983

[30] Foreign Application Priority Data

Sep. 28, 1982 [FR] France .................. 82 16303

[51] Int. Cl.[4] ............................ G01N 27/74
[52] U.S. Cl. .................................. 324/204
[58] Field of Search ................ 324/459, 204; 73/61.1 C

[56] References Cited

U.S. PATENT DOCUMENTS

| 2,779,917 | 1/1957 | De Boisblanc | 324/204 |
| 3,076,929 | 2/1963 | Gillerman | 324/204 |
| 3,292,077 | 12/1966 | Sloughter | 324/204 X |
| 3,404,336 | 10/1968 | Rosenthal | 324/30 |
| 4,138,639 | 2/1979 | Hutchins | 324/30 |
| 4,464,926 | 8/1984 | Albarda et al. | 324/204 X |

FOREIGN PATENT DOCUMENTS

| 1281567 | 10/1968 | Fed. Rep. of Germany . |
| 2822943 | 11/1979 | Fed. Rep. of Germany . |
| 3030069 | 3/1982 | Fed. Rep. of Germany . |
| 995035 | 2/1983 | U.S.S.R. | 324/204 |

OTHER PUBLICATIONS

Ogren, V. G. *Sensor Circuit Utilizing Variable Inductance Input,* IBM Tech. Discl. Bulletin, vol. 14, No. 4, Sep. 1971.
Bunyak et al., Resonant LC Circuit as a Contactless Conductometric Converter, Measurement Techniques vol. 17, No. 11, published Apr. 1975.

*Primary Examiner*—Stewart J. Levy
*Assistant Examiner*—Joseph W. Roskos
*Attorney, Agent, or Firm*—Scully, Scott, Murphy & Presser

[57] ABSTRACT

A detector of ion concentration in a liquid is composed of a detection cell comprising a tubular piece formed from an electrically insulating material with a central passage which is fed with a liquid whose ion concentration is to be measured. A conducting coil is placed around the tubular piece, and is part of a first resonant circuit. A second reference resonant circuit is also provided, and signals of fixed frequency are applied in parallel to the two resonant circuits, and a comparator delivers a signal having a magnitude representative of the difference between the output signals from the two resonant circuits. Such a detector finds a use for example in liquid chromatography.

3 Claims, 1 Drawing Figure

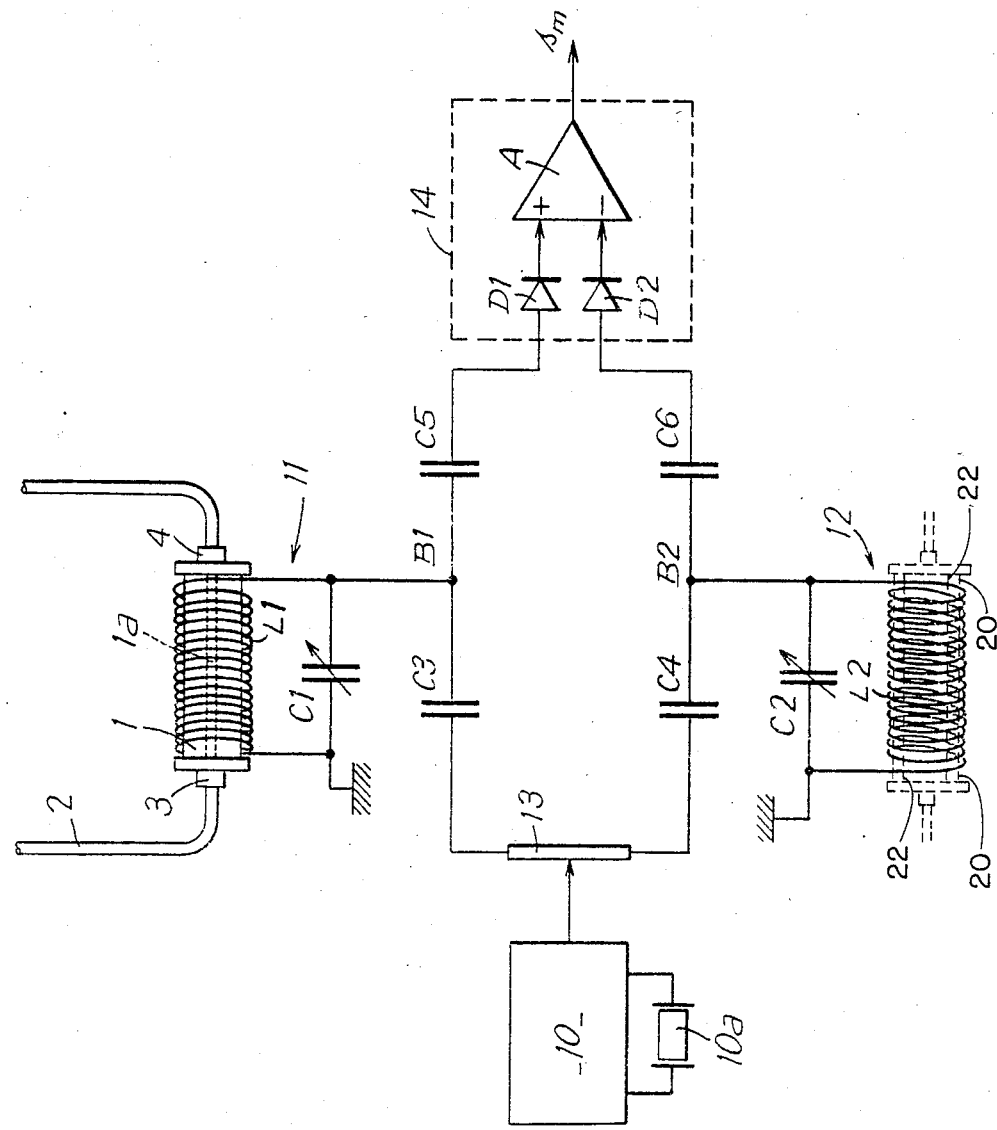

DETECTION OF ION CONCENTRATION IN A LIQUID

The present invention relates to a detector of ion concentration in a liquid.

The present invention is particularly but not exclusively applied to the detection of ion concentration or strength in an aqueous solution coming out of a chromatographic column.

In this field, it has already been proposed to produce detectors of ion or salt concentration of the conductimetric type measuring the conductivity variations of the liquid flowing through a measuring probe. It has also been proposed to measure the dielectric constant variations of the liquid, by directing said liquid between two plates forming condenser plates, the capacity variations of which are detected for example by measuring the resonance frequency of an oscillating circuit of which said condenser forms part.

In all these known apparatuses, the liquid is in contact with the electrodes between which there is a potential difference. It is not always possible to prevent phenomena of electrolysis which could perturb the detection or alter the characteristics of the liquid, this being a great disadvantage especially in chromatography.

It is the object of the present invention to propose a detector capable of producing a measuring signal representing precisely the ion concentration or strength of a liquid, such as a salt solution, without being in contact with said liquid.

This object is reached with a detector which, according to the invention, comprises:

- a detection cell consisting in a tubular piece made from an electrically insulating material with a central passage adapted to be fed with the liquid whose ion concentration is to be measured, and
- an electric circuit including an oscillator for generating a signal having a fixed frequency, a first resonant circuit comprising a conducting coil placed around said tubular piece and excited by the oscillator output signal, a second reference resonsant circuit also energized by the oscillator output signal, and a comparator receiving the signals produced by the two resonant circuits and delivering a signal whose amplitude represents the difference between the signals that it receives.

By using a resonant circuit of reference, it is possible to avoid the influence of certain characteristics of the circuits which vary with respect to external conditions, in particular the temperature.

The invention will be more readily understood on reading the following description with reference to the accompanying drawing in which the one and only FIGURE illustrates diagrammatically a special embodiment of a detector according to the invention.

The liquid of which the ion concentration or strength is to be measured, for example a liquid containing an aqueous salt solution coming out of a chromatographic column, flows through the central passage $1a$ of a tubular piece 1 forming detection cell. Said piece 1 is made from a non-conducting material, such as glass for example, and is interposed on a conduit 2 to which it is connected via coupling 3,4.

A coil L1 is placed around the piece 1 and is connected in parallel to a capacitor C1 of adjustable capacity, to form a first resonant circuit 11. Another coil L2, of similar dimensions as L1 is connected in parallel to a capacitor C2 of adjustable capacity, to form a second resonant circuit 12.

Circuits 11, 12 are connected between respective terminals B1, B2 and a terminal of reference potential (ground). Terminals B1, B2 are coupled via respective capacitors C3, C4 and a voltage divider 13 to the output of an oscillator 10. Said latter issues a signal of fixed high frequency, stabilized by a quartz clock $10a$. Said frequency is for example between 10 and 100 MHz. Said divider 13 is for example of a resistive type and is designed to transmit the oscillator output signal symmetrically on the two branches comprising the circuits 11 and 12.

Terminals B1 and B2 are moreover coupled via respective capacitors C5, C6 to the inputs of a comparator circuit 14. Said circuit includes detection means, for example with diodes D1, D2 connected between the terminals B1, B2 and the respective inputs of a differential amplifier A. A measuring signal $s_m$ is outputted from said differential amplifier A, which signal represents the difference between the amplitudes of the signals applied to its inputs, namely, in this particular case, a signal representing the amplitude difference between the signals available at terminals B1 and B2.

The detector described hereinabove works as follows.

When the ion concentration of the liquid contained in the tubular piece 1 varies, the self-inductance of the coil L1 varies correspondingly and as a result the resonant frequency of the circuit 11. The amplitude of the signal on terminal B1 also varies. The capacity of capacitor C1 is adjusted so that the amplitude of the signal in terminal B1 varies uniformly (increasingly or decreasingly) within the range of concentrations to be measured. In other words, said capacity is adjusted so that the possible range of variation of the resonant frequency of the circuit 11 is situated on one side of and close to the frequency of oscillator 10.

Said resonant circuit 12 supplies at B2 a reference voltage to which the voltage at B1 is compared so that the signal $s_m$ represents the concentration of the liquid inside the tube 1. To adjust the zero output of the detector, it suffices to feed de-ionized water to the tube and to adjust the capacity of capacitor C2.

With a detector such as illustrated in the FIGURE, it has been found that the relation between the amplitude of signal $s_m$ and the ionic concentration is of the logarythmic type.

One important advantage of the detector according to the invention resides in the fact that the liquid whose ion concentration is to be measured is not in conact with electrodes but that it is merely subjected to an alternating field of high frequency and optionally very low power.

It will be noted that for a given length, the diameter of passage $1a$ determines the sensitivity of the detector. The larger this diameter, the greater the sensitivity. By way of indication, it is possible with a detection cell having a passage of 20 mm length and 0.5 mm diameter to measure NaCl concentrations of, for example, between 0 and 2M, whereas with a cell with a passage of the same length but of 2 mm diameter, it is possible to measure NaCl concentrations of between 0 and 0.1M.

According to a variant embodiment, the detector according to the invention can comprise two detection cells with central passages of different dimensions, one cell 1 being provided with the coil L1 and the other cell 20 (shown in dashed lines in the drawing as an alternative embodiment with a larger central passage 22) with the coil L2. Depending on the required sensitivity, one of the cells is fed with the liquid to be measured for concentration, the other being used as reference, its central passage being optionally filled with the de-ionized water. Each one of circuits 11 and 12 can then be used as a circuit of variable frequency and resonance, or as a reference circuit, means being then provided to reverse the connections between said circuits and the comparator circuit.

What we claim is:

1. Detector of ion concentration in a liquid comprising:
    a detection cell consisting of a tubular piece made from an electrically insulating material with a central passage through which the liquid whose ion concentration is to be measured is to flow, and
    an electric circuit including an oscillator for generating a signal having a fixed frequency, a first resonant circuit comprising a conducting coil placed around said tubular piece, a second reference resonant circuit, said first and second resonant circuits being connected in parallel to the oscillator to be energized by the output signal thereof, and a comparator having a first and a second inputs for receiving the signals produced respectively by the first and second resonant circuits and delivering a signal whose amplitude represents the difference between the signals that it receives.

2. Detector as claimed in claim 1, wherein the resonance frequency of the first resonant circuit varies as a function of the salt concentration of the liquid contained in the tubular piece within a frequency range having a limit situated close to the oscillator fixed frequency, the latter being outside, said frequency range.

3. Detector as claimed in claim 1, wherein the second resonant circuit comprises a coil wound around a second tubular piece the central passage of which differs in dimensions from the central passage of the first tubular piece, thus forming first and second detection cells of different sensitivity, each of which cells can be fed with the liquid whose ion concentration is to be measured, or with reference liquid.

* * * * *